United States Patent [19]

Parnell

[11] Patent Number: 4,938,963

[45] Date of Patent: Jul. 3, 1990

[54] METHOD AND COMPOSITION FOR TREATING XEROSTOMIA

[75] Inventor: Francis W. Parnell, Ross, Calif.

[73] Assignee: Parnell Pharmaceuticals, Inc., San Rafael, Calif.

[21] Appl. No.: 275,124

[22] Filed: Nov. 22, 1988

[51] Int. Cl.⁵ .................... A61K 9/20; A61K 35/78; A61K 9/68

[52] U.S. Cl. .................................... 424/440; 424/48; 424/195.1; 424/464

[58] Field of Search .................... 424/195.1, 48, 440, 424/464

[56] References Cited

U.S. PATENT DOCUMENTS

| | | | |
|---|---|---|---|
| 4,029,815 | 6/1977 | Sherlock et al. | 514/615 X |
| 4,151,270 | 4/1979 | Ream et al. | 424/48 |
| 4,209,505 | 6/1980 | Mikhail | 424/54 |
| 4,438,100 | 3/1984 | Balslev et al. | 424/104 |

OTHER PUBLICATIONS

Fukuda et al., *Chemical Abstracts*, 93, 69113b (1980).
Viktorova et al., *Chemical Abstracts*, 96, 33644y (1982).
Sato et al., *Chemical Abstracts*, 104, 108262a (1986).
Hawley, *The Condensed Chemical Dictionary*, Tenth Edition, pp. 253-254 (1981).
*The Merck Index*, Tenth Edition, p. 530 (1983).
Lust, *The Herb Book*, p. 407 (1974).
Steinmetz, *Codex Vegetabilis*, p. 429 t/m 436 (1957).
N. Coon, *The Dictionary of Useful Plants*, Emmaus, Pa.: Rodale Press, 1974, pp. 20, 152.
N. Coon, *Using Plants for Healing*, Hearthside Press, 1963, p. 122.
P. C. Fox et al., *J. Am. Dental Assoc.*, 110:519-525 (1985).
M. Grieve, *A Modern Herbal*, vol. II, New York: Hafner Publishing Co., 1959, p. 865.
B. C. Harris, *The Compleat Herbal*, Barre, Mass.: Barre Publishers, 1972, p. 197.
P. Huson, *Mastering Herbalism: A Practical Guide*, New York: Stein and Day, 1974, p. 32.
A. R. Hutchens, *Indian Herbalogy of North America*, Ontario: Merco, 1975, pp. 317-318.
W. H. Lewis et al., *Medical Botany: Plants Affecting Man's Health*, New York: John Wiley & Sons, 1977, p. 301.
M. Moore, *Los Remedios de la Gente: A Compilation of Traditional New Mexican Herbal Medicines and Their Use*, Santa Fe, N.M.: Herbs-Etc., 1977, p. 17.
D. G. Spoerke, *Herbal Medications*, Santa Barbara, Calif.: Woodbridge Press, 1980, pp. 183, 185-186.
G. E. Trease et al., *Pharmacognosy*, London: Cassell & Colber, 1978, p. 463.
V. E. Tyler et al., *Pharmacognosy*, Philadelphia: Lee & Febiger, 1981, p. 148.
V. J. Vogel, *American Indian Medicine*, The University of Oklahoma Press, 1970, pp. 83, 399-400, 469-470.

*Primary Examiner*—John W. Rollins
*Assistant Examiner*—W. Catchpole
*Attorney, Agent, or Firm*—Irell & Manella

[57] ABSTRACT

Methods and compositions are provided for alleviating xerostomia. The compositions are formulated from Yerba Santa extract and sweetener, and may be in aqueous solution or in gum or lozenge form. The compositions may additionally contain a stimulator compound effective to stimulate salivary gland secretion, e.g., citric acid, ascorbic acid, or both. Preservatives, flavoring agents, coloring agents, emulsifiers, and the like may be included in the compositions as well. The Yerba Santa-based compositions of the invention are orally administered to an affected patient to alleviate the symptoms of dry mouth.

19 Claims, No Drawings

METHOD AND COMPOSITION FOR TREATING XEROSTOMIA

TECHNICAL FIELD

The invention relates generally to xerostomia, commonly known as "dry mouth syndrome". More particularly, the invention relates to a novel composition for alleviating the symptoms of xerostomia in an affected patient. The active ingredient of the novel composition is Yerba Santa fluid extract.

The invention also encompasses a method of treating xerostomia comprising administering a Yerba Santa-based composition to an affected individual.

BACKGROUND

Xerostomia is a condition in which the salivary glands do not produce sufficient quantities of saliva. This causes discomfort which can in some cases be quite severe. Without saliva, the mouth burns and the throat and tongue can undergo radical changes. Teeth can decay rapidly and the tongue can become smooth, cracked and vulnerable to infection. There is often a loss of taste and, because saliva contains important digestive enzymes, there are often problems with digestion.

The mouth is one of the body areas most exposed to the external environment. Normally, mucous forms a continuous protective layer in the nose, mouth and throat. A patient suffering from xerostomia not only has decreased fluid in the mouth, but also an insufficient quantity of mucoproteins and mucopolysaccharides to hold fluid in contact with the cells and create a barrier to irritation and infection.

It is estimated that several million individuals suffer from this condition nationwide. The actual number of individuals suffering from xerostomia is not known, however, because until recently there has been little acknowledgement of the prevalence or severity of the problem.

Cases of xerostomia may vary from the mild, in which only slight dryness is experienced, to severe cases in which the patient will have serious problems with mastication, swallowing, digestion, speech, and the like. As noted in U.S. Pat. No. 4,438,100 to Balslev et al., there are a number of causes of xerostomia, including the physiological (e.g., age, menopause, postoperative conditions, dehydration), as well as the psychic (nervousness). The reasons for mouth dryness may also be pharmacological (e.g., as a common side effect of many medications, including diuretics, anti-arthritics and anti-depressants) or as a result of radiotherapy. The most severe cases of xerostomia are caused by radiation therapy after head and neck surgery and by autoimmune diseases such as lupus, Sjogrens Syndrome, and rheumatoid arthritis. See, for example, P.C. Fox et al., *J. Am. Dental Assoc.* 110:519-525 (1985).

Until recently, the treatments for xerostomia have had significant drawbacks. For example, symptoms of mild xerostomia can be somewhat alleviated by consumption of fluids, hard candy and throat lozenges. Because of the susceptibility of xerostomia patients to tooth decay and gum disease, however, the increased sugar intake associated with conventional candy and lozenges is of real concern. In addition, fluids or candy are typically not effective with more severe cases of xerostomia, nor do they provide long-lasting relief with mild cases.

There are also a number of artificial salivas on the market which contain alcohol, mineral oils, glycerine, and combinations of polyethylene glycols. A number of carboxymethylcellulose-based preparations are on the market as well, including those sold under the marks Orex ® (Young Dental), Xero-Lube ® (Scherer), Mci-Stir ® (Kingswood Laboratories), and Salivart ® (Westport Pharmaceuticals). Many patients find, however, that such preparations are irritating or distasteful, and that their lubricating effect is of relatively short duration.

There has also been some experimentation with parasympathomimetic drugs, i.e., drugs that mimic the action of the parasympathetic nervous system which controls salivation. There have been reported dosage control problems with these drugs, however, as well as significant side effects.

The present invention is premised on the surprising discovery that the oil extracted from the Yerba Santa plant (*Eriodictyon californicum; Eriodictyon glutinosum*; also known as "consumptive's weed"; "bear's weed" "mountain balm" and "gum plant") is extremely effective in providing long-lasting relief in cases of mild to severe xerostomia, with no unpleasant side effects.

The Yerba Santa plant is an evergreen shrub indigenous to the hills and mountains of California and northern Mexico, and was long used by Indians for a number of purposes. See, e.g., A.R. Hutchens, *Indian Herbalogy of North America*, Ontario: Merco, 1975, at pp. 317-318. A number of references to the Yerba Santa plant teach its use as an expectorant (e.g., N. Coon, *The Dictionary of Useful Plants*, Emmaus, Pa.: Rodale Press, 1974)), in treating colds, sore throats, catarrh, stomach aches, vomiting and diarrhea (see A.R. Hutchens, supra), in treating hemorrhoids (D.G. Spoerke, *Herbal Medications*, Santa Barbara, CA: Woodbridge Press, 1980, at p. 183), in treating diseases of the lung (*Los Remedios de la Gente: A Compilation of Traditional New Mexican Herbal Medicines and Their Use*, compiled by M. Moore, 1977), and in masking the taste of quinine and other bitter medications (Spoerke, supra; see also G.E. Trease et al., *Pharmacognosy*, London: Cassell & Colber, 1978, at p. 463)). However, the discovery that Yerba Santa is effective in significantly alleviating xerostomia is novel and completely unsuggested by the art.

Description of the Prior Art

Relevant background references on the Yerba Santa plant include the Coon, Hutchens, Moore, Spoerke, and Trease et al. references, cited in the preceding section, as well as V.J. Vogel, *American Indian Medicine*, The University of Oklahoma Press, 1970, at pp. 83, 399-400; W.H. Lewis et al., *Medical Botany: Plants Affecting Man's Health*, New York: John Wiley & Sons, 1977, at p. 301; P. Huson, *Mastering Herbalism: A Practical Guide*, New York: Stein and Day, 1974, at p. 32; B.C. Harris, *The Compleat Herbal*, Barre, Massachusetts: Barre Publishers, 1972, at p. 197; N. Coon, *Using Plants for Healing*, Hearthside Press, 1963, at p. 122; M. Grieve, *A Modern Herbal*, vol. 22, New York: Hafner Publishing Co., 1959, at p. 865; and V.E. Tyler et al., *Pharmacognosy*, Philadelphia: Lee & Febiger, 1981, at p. 148.

An informative background reference on xerostomia is P.C. Fox et al. (1985), *J. Am. Dental Assoc.* 110:519-525 (1985).

The following references relate to compositions and methods for treating xerostomia:

U.S. Pat. No. 4,438,100 to Balslev et al. discloses a viscous artificial saliva containing a mucine and an oxidizing bacteriocide.

U.S. Pat. No. 4,209,505 to Mikhail discloses a mouthwash for dry mouth relief, containing pilocarpine or a pilocarpine derivative. It is also noted therein notes that various types of diets have also been used (albeit unsuccessfully) in an attempt to alleviate xerostomia.

U.S. Pat. No. 4,151,270 to Ream et al. teaches a chewing gum composition formulated to stimulate salivation. The gum contains fructose and an organic acid such as adipic, ascorbic, citric, fumaric, lactic, malic or tartaric acids.

Summary of the Invention

It is a primary object of the present invention to overcome the above-mentioned difficulties in the art.

It is another object of the invention to provide a method for treating xerostomia, comprising orally administering, to an affected individual, an amount of a Yerba Santa composition effective to alleviate the symptoms of dry mouth, the Yerba Santa composition comprising Yerba Santa extract and sweetener.

It is still another object of the invention to provide such a method wherein the composition to be administered contains Yerba Santa fluid extract and a sweetener either in an aqueous solution or in gum or lozenge form.

It is yet another object of the invention to provide such a method wherein the composition to be administered, in addition to containing Yerba Santa fluid extract and sweetener, includes a stimulator compound effective to stimulate salivary gland secretion.

It is a further object of the invention to provide such a method wherein the composition to be administered contains Yerba Santa fluid extract, sweetener, citric acid, ascorbic acid, and a preservative.

It is still a further object of the invention to provide a Yerba Santa-based composition for treating xerostomia, useful in the aforementioned method.

It is yet a further object of the invention to provide a composition for treating xerostomia which contains Yerba Santa fluid extract, sweetener, citric acid, ascorbic acid, and a preservative.

In one aspect of the invention, the method for alleviating xerostomia comprises administering an aqueous solution of Yerba Santa fluid extract to a patient. The composition may also be administered in gum or lozenge form. In addition to Yerba Santa fluid extract, the composition also contains one or more sweeteners which are preferably noncariogenic. In a preferred embodiment of the invention, the composition additionally contains citric acid and/or ascorbic acid to stimulate salivary gland secretion, provide flavor, and aid in effecting solution of the Yerba Santa fluid extract (where the composition is in the form of an aqueous solution).

DETAILED DESCRIPTION OF THE PREFERRED EMBODIMENTS

In its broadest sense, the invention encompasses a method of treating xerostomia by administration of a sweetened composition of Yerba Santa fluid extract to an affected patient. By "Yerba Santa fluid extract" as used herein is meant the fluid which may be extracted from dried Yerba Santa leaves. One exemplary method for obtaining Yerba Santa fluid extract is set forth in *Remington's Pharmaceutical Sciences*, 17th Ed., 1985, at pp. 1286 and 1516. As described in detail therein, the dried Yerba Santa plant is preferably processed in alcohol and water, followed by straining, pressing and clarification by, e.g., decantation or filtration.

In a preferred embodiment, the composition is administered as an aqueous solution of Yerba Santa fluid extract and one or more sweeteners. The composition will preferably contain in the range of 0.25 wt.% to 10 wt.%, more preferably 0.5 wt.% to 5.0 wt.%, and most preferably about 1.25 wt.% Yerba Santa fluid extract. The composition will also contain one or more sweeteners, in total comprising about 1.0 wt.% to 30 wt.%, more preferably 10 wt.% to 20 wt.%, most preferably about 15 wt.% sweetener.

Suitable sweeteners may be readily selected by those skilled in the art, and the amount of sweetener incorporated into the present composition will be determined by taste. Generally, the sweetener may be any compound or compounds that cause sweetness or intensify sweetness. The sweetener may be of naturally occurring or synthetic origin, and may have nutritive or non-nutritive value. Examples of suitable sweeteners for use herein include: the saccharides, e.g., fructose, glucose, glycerose, threose, erythrose, methylpentose, galactose, xylose, ribose, dextrose, maltose and d-mannose; sugar alcohols such as sorbitol, xylitol and mannitol; water-soluble artificial sweeteners such as the soluble saccharin salts, e.g., sodium or calcium saccharin, cyclamate salts, acesulfame-K, and the like; and dipeptide-based sweeteners such as L-aspartyl-L-phenylalanine methyl ester. Other examples of suitable sweeteners are set forth in the *Encyclopedia of Chemical Technology*, vol. 19, 2d Ed , New York: John wiley & Sons, 1969, at pp. 593–607. Preferred sweeteners are noncariogenic, and particularly preferred sweeteners for use herein are xylitol, sorbitol, mannitol, sodium saccharin, and combinations thereof.

It is preferred that the composition also contain a "stimulator" compound which will stimulate salivary gland secretion. A particularly preferred compound for this purpose is citric acid, present in an amount ranging from about 0.25 wt.% to about 5.0 wt.%, preferably about 0.5 wt.%. Incorporation of citric acid into the present composition also serves to provide a pleasant, citrus flavor and to facilitate solubilization of the resinous Yerba Santa fluid extract.

Another compound which has been found to help solubilize the Yerba Santa extract and stimulate salivary gland secretion is ascorbic acid, which is preferably present in an amount ranging from 0.01 to 1.0 wt.%. The ascorbic acid may be present in addition to, or as an alternative to, the citric acid. In a preferred embodiment, both citric acid and ascorbic acid are present.

It is preferred that the composition contain one or more preservatives, typically an anti-oxidant present in an amount effective to retard oxidation and/or inactivation of the fluid extract. As with sweeteners, the selection of a preservative or preservatives will be readily made by one skilled in the art. Examples of suitable preservatives include ascorbyl palmitate, butylated hydroxyanisole, butylated hydroxytoluene, potassium or sodium sorbate, sodium bisulfite, sodium metabisulfite, sorbic acid, sulfur dioxide, and sodium or potassium benzoate. A particularly preferred preservative for use herein is sodium benzoate.

Other components which may, if desired, be incorporated into the present composition include coloring agents, which may be either natural or synthetic, flavoring agents, flavor preserving agents, diluting agents, emulsifying agents, excipients, pH buffering agents, and the like.

Suitable colorants include dyes that are generally suitable for food, drug and cosmetic applications, i.e., those known as "F.D. & C." dyes. Where the Yerba Santa composition is in aqueous form, acceptable dyes should be water soluble. Illustrative examples include the disodium salt of 5,5-indigotindisulfonic acid ("F.D. & C. Blue No. 2.") and the monosodium salt of 4-[4-N-ethyl-p-sulfo-benzylamino)diphenylmethylene]-[1-(N-ethyl-N-p-sulfonium-benzyl)-2,5-cyclohexadienimine ("F.D. & C. Green No. 1"). Reference may be had to the Kirk-Othmer Encyclopedia of Chemical Technology, 3rd Ed., in Volume 6, for further F.D.& C. colorants and corresponding chemical structures.

Flavorings are optional, as incorporation of citric and/or ascorbic acids into the composition will in the absence of any additional flavoring agents provide a pleasant, citrus flavor. Additional flavorings may include other natural or artificial flavors, e.g., mint oils such as peppermint, wintergreen (methyl salicylate), spearmint, eucalyptus, etc., citrus oils such as lemon oil, orange oil, lime oil, grapefruit oil, fruit essences such as apple essence, peach essence, raspberry essence, and the like. Where an oil-based flavoring agent is selected, one or more preservatives will be included in the composition as described above. Various synthetic flavors may also incorporated into the composition. The flavoring agent(s) will be present in an amount depending on the individual agent selected, but, if present, will typically range from about 0.5 wt.% to about 5.0 wt.% of the composition.

The composition as just described is preferably administered as an aqueous solution, which is readily prepared by admixing the Yerba Santa fluid extract with the remaining selected components in water.

The composition may also be prepared as a gum or lozenge, with the preferred components and the preferred relative composition by weight the same as in the above-described aqueous solution.

Yerba Santa-based gum compositions are prepared using conventional means. The Yerba Santa extract is admixed with a chewable gum base, one or more sweeteners, and optional additional components as described hereinabove, present in the above-described proportions. The gum composition will also typically include flavoring additives, emulsifying agents, and coloring agents as described above.

The "gum base" may be one of a number of types of compositions, and is typically prepared by heating and blending various ingredients, e.g., natural gums, synthetic resins, waxes, plasticizers, etc. Typical examples of the ingredients found in a chewing gum base include masticatory substances of vegetable origin such as chicle, crown gum, nispero, rosidinha, jelutong, pendare, perillo, niger gutta, tunu, etc., masticatory substances of synthetic origin such as butadiene-styrene polymer, isobutyleneisoprene copolymer, paraffin, petroleum wax, polyethylene, polyisobutylene, polyvinylacetate, etc., plasticizers or softeners such as lanolin, stearic acid, sodium stearate, potassium stearate, glyceryl triacetate, glycerine, etc.

Waxes, including natural and synthetic waxes, petroleum waxes, paraffin waxes and microcrystalline waxes may also be incorporated into the gum base in order to obtain desirable texture and consistency.

Lozenges will typically be shaped solids containing the resinous Yerba Santa fluid extract in a candy or glycerinated gelatin base. Preparation of lozenge forms is well known in the art, and is described, for example, in Remington's Pharmaceutical Sciences, cited supra, at page 1631. Typically, the Yerba Santa extract is mixed with sweetener and other optional compounds as described above. The resulting syrup is concentrated and the mixture shaped and/or compressed, while heating, into the desired form.

The amount of Yerba Santa extract administered will, of course, be dependent on the subject being treated, the severity of the xerostomia, and the judgment of the prescribing health care professional. However, an effective dosage regimen will typically be 1–2 tsp of an aqueous composition (or the equivalent in gum or lozenge form) containing 0.25 wt.% to 10 wt.% Yerba Santa fluid extract, given orally 4–6 times per day. This is approximately equivalent to 1.0 to 6.0 g Yerba Santa fluid extract in a twenty-four hour period. For the aqueous composition, it is preferred that the composition be retained in contact with the oral mucosa for a time sufficient to allow coating of the interior of the mouth with the Yerba Santa fluid extract. It is preferred that the composition be retained in the mouth for 8–10 seconds. The composition may be administered as a mouthwash, where the mouth is simply rinsed with the aqueous solution, or if desired, the composition may be swallowed. When the composition is administered in gum or lozenge form, again, an approximate daily dose of 1.0 to 6.0 g. Yerba Santa fluid extract is optimal.

It is to be understood while the invention has been described in conjunction with the preferred specific embodiments thereof, that the foregoing description as well as the example which follows are intended to illustrate and not limit the scope of the invention.

EXAMPLE

| Ingredients | Quantity |
| --- | --- |
| Water | 72.25 wt. % |
| Xylitol | 15.00 wt. % |
| Sorbitol | 10.0 wt. % |
| Yerba Santa Fluid Extract* | 1.25 wt. % |
| Citric Acid | 0.50 wt. % |
| Flavor | 0.50 wt. % |
| Ascorbic Acid | 0.25 wt. % |
| Sodium Benzoate | 0.25 wt. % |

*Dried eriodictyon was obtained from Meer Corporation, North Bergen, New Jersey. The fluid extract was prepared therefrom substantially as described in Remington's Pharmaceutical Sciences, 17th Ed., cited supra, on pages 1286 and 1516.

After preparation of the fluid extract, the above ingredients were mixed to give an aqueous solution of sweetened Yerba Santa fluid extract.

One to two teaspoons of the above solution were administered several times a day to 125 patients having mild to severe xerostomia. After one week, over 70% of the patients showed marked improvement.

I claim:

1. A method for treating xerostomia, comprising orally administering, to an affected individual, an amount of an eriodictyon fluid composition effective to alleviate the symptoms of dry mouth, the eriodictyon fluid composition comprising eriodictyon fluid extract and sweetener.

2. The method of claim 1, wherein the eriodictyon fluid composition is an aqueous solution of eriodictyon fluid extract and sweetener.

3. The method of claim 2, wherein the composition contains about 0.25 wt.% to 10 wt.% eriodictyon fluid extract.

4. The method of claim 3, wherein the composition contains about 0.5 wt.% to 5 wt.% eriodictyon fluid extract.

5. The method of claim 1, wherein the eriodictyon fluid composition additionally includes a stimulator compound effective to stimulate salivary gland secretion.

6. The method of claim 5, wherein the stimulator compound is selected from the group consisting of citric acid, ascorbic acid and mixtures thereof.

7. The method of claim 6, wherein the composition contains about 0.25 wt.% to about 5.0 wt.% citric acid and about 0.01 wt.% to about 1.0 wt.% ascorbic acid.

8. The method of claim 1, wherein the composition contains about 1.0 wt.% to 30 wt.% sweetener.

9. The method of claim 8, wherein the composition contains about 10 wt.% to 20 wt.% sweetener.

10. The method of claim 9, wherein the composition contains about 15 wt.% sweetener.

11. The method of claim 1, wherein the Yerba Santa composition is administered in the form of a lozenge.

12. The method of claim 11, wherein the lozenge contains about 0.25 wt.% to about 10 wt.% eriodictyon fluid extract and about 1 wt.% to about 30 wt.% sweetener.

13. The method of claim 1, wherein the eriodictyon fluid composition is administered in the form of a gum.

14. The method of claim 1, wherein the gum contains about 0.25 wt.% to 10 wt.% eriodictyon fluid extract and about 1 wt.% to 30 wt.% sweetener.

15. A method for treating xerostomia, comprising orally administering, to an affected individual, an amount of an eriodictyon fluid composition effective to alleviate the symptoms of dry mouth, the eriodictyon fluid composition comprising about 0.25 wt.% to 10 wt.% eriodictyon fluid extract, about 1.0 wt.% to 30 wt.% sweetener, and a stimulator compound effective to stimulate salivary gland secretion.

16. The method of claim 15, wherein the stimulator compound is selected from the group consisting of citric acid, ascorbic acid and mixtures thereof.

17. The method of claim 16, wherein the composition contains about 0.25 wt.% to about 5.0 wt.% citric acid and about 0.01 wt.% to about 1.0 wt.% ascorbic acid.

18. The method of claim 1, wherein the eriodictyon fluid composition is administered such that an individual receives about 0.25 to 1.0 g. eriodictyon fluid extract four to six times in a twenty-four hour period.

19. The method of claim 15, wherein the eriodictyon fluid composition is administered such that an individual receives about 0.25 to 1.0 g. eriodictyon fluid extract four to six times in a twenty-four hour period.

* * * * *